United States Patent
Norman

(10) Patent No.: US 8,859,785 B2
(45) Date of Patent: Oct. 14, 2014

(54) VOLATILE GROUP 2 METAL PRECURSORS

(75) Inventor: John Anthony Thomas Norman, Encinitas, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 1087 days.

(21) Appl. No.: 12/785,041

(22) Filed: May 21, 2010

(65) Prior Publication Data

US 2011/0120875 A1    May 26, 2011

Related U.S. Application Data

(60) Provisional application No. 61/182,186, filed on May 29, 2009.

(51) Int. Cl.
*C07D 207/46* (2006.01)
*C07F 3/00* (2006.01)

(52) U.S. Cl.
CPC .................................. *C07F 3/003* (2013.01)
USPC ........................................ 548/518; 548/510

(58) Field of Classification Search
USPC .................................................. 548/402, 518
See application file for complete search history.

(56) References Cited

U.S. PATENT DOCUMENTS 5,319,118 A * 6/1994 Norman et al. ................... 556/2
2005/0240028 A1 10/2005 Grushin

FOREIGN PATENT DOCUMENTS

| CN | 1688741 A | 10/2005 | |
|---|---|---|---|
| KR | 2001-0079799 A | 8/2001 | |
| WO | 2009/086263 A1 | 7/2009 | |
| WO | WO-2009/086263 | * 7/2009 | ................ C07F 3/00 |

OTHER PUBLICATIONS

Schumann et al, "Synthesis and structure of n5-bonded pyrrolyl complexes of calcium and strontium," Chem Comm. (1999), pp. 2091-2092.*
Schumann, H. et al; "Synthesis and Structure of Eta-5-Bonded Pyrrolyl Complexes of Calcium and Strontium"; Chemical Communications; 1999; pp. 2091-2092; XP002595284.
Westerhausen, M. et al; "2,5-Diphenyl-3,4-Bis(Trimethylsilyl)-1-Phosphacyclopentadienide as a Ligand at Calcium, Strontium and Tin (II)"; Inorganic Chemistry; vol. 38, No. 13; 1999; pp. 3207-3214; XP002595285.
Hani M. El-Kaderi, et al., Sandwich Complexes of the Heavier Alkaline Earth Metals Containing B—Diketiminato Ligand Sets, 2004, 23 (21), 4995-5002.
Baburam Sedai, et al., Volatility Enhancement in Calcium, Strontium, and Barium Complexes Containing B—Diketiminate Ligands with Dimethylamino Groups on the Ligand Core Nitrogen Atoms, 2009, 28, 1032-1038.
Timo Hatanpaa, et al., Synthesis and Characterisation of Cyclopentadienyl Complexes of Barium: Precursors for Atomic Layer Deposition of BaTiO3 (2004) p. 1181-1188.

(Continued)

*Primary Examiner* — Kamal Saeed
*Assistant Examiner* — Janet L Coppins
(74) *Attorney, Agent, or Firm* — Rosaleen P. Morris-Oskanian; Joseph D. Rossi

(57) ABSTRACT

A compound comprising one or more polyfunctionalized pyrrolyl anions coordinated to a metal selected from the group consisting of barium, strontium, magnesium, radium or calcium or mixtures thereof. Alternatively, one anion can be substituted with and a second non-pyrrolyl anion.
Synthesis of the novel compounds and their use to form BST films is also contemplated.

11 Claims, 11 Drawing Sheets

(56) References Cited

OTHER PUBLICATIONS

Norbert Kuhn, et al., On the Silylation of Sterically Overcrowded Pyrroles, J. Prakt. Chem. 335 (1993) 285-287.

Herbert Schumann, et al., Synthesis and Structure of N5-bonded pyrrolyl complexes of calcium and strontium, Chem. Commun., (1999), p. 2091-2092.

J. A. T. Norman, et al., Volatile Barium, Strontium and Calcium Bis(hexafluoroacetylacetonate) (crown ether) Complexes, J. Chem. Soc., Chem. Commun., (1991) p. 971-972.

Brian A. Vaartstra, et al., Syntheses and Structures of a Series of Very Low Coordinate Barium Compounds: Ba[N(SiMe3)2]2(THF)2, {Ba[N(SiMe3)2]2(THF)}2, and {Ba[N(SiMe3)2]2}2, Inorg. Chem. (1991), 30, 121-125.

Sjoerd Harder, et al., Homoleptic B—Diketiminato Complexes of the Alkaline-Earth Metals: Trends in the Series Mg, Ca, Sr, and Ba, Organometallics (2002), 21, 3782-3787.

R. Ramasseul, et al., Synthesis of 2,5-Di-t-butylpyrrole and of 2,3,5-Tri-t-butylpyrrole, Chem Comm. (1965) p. 453.

Mark J. Saly, et al., Volatility, High Thermal Stability, and Low Melting Points in Heavier Alkaline Earth Metal Complexes Containing Tris(pyrazolyl)borate Ligands, (Web): Apr. 27, 2009.

Schumann, et al.; "Synthesis and Structure of n-bonded Pyrrolyl Complexes of Calcium and Strontium"; Chemical Communications; 1999; vol. 20; pp. 2091-2092.

Westerhausen, et al.; "2,5-Dyphenyl1-3,4-Bis (Trimethylsilyl)-1-Phosphacyclopentradienide as a Ligand at Calcium, Strontium, and Tin(II)"; Inorganic Chemistry; 1999; vol. 38, No. 13; pp. 3207-3214.

* cited by examiner

VOLATILE GROUP 2 METAL PRECURSORS

CROSS REFERENCE TO RELATED APPLICATION

The present application claims the benefit of U.S. Provisional Patent Application Ser. No. 61/182,186 filed May 29, 2009.

BACKGROUND OF THE INVENTION

The semiconductor fabrication industry continues to source volatile metal containing precursors for vapor deposition processes, including chemical vapor deposition (CVD) and atomic layer deposition (ALD), for fabricating conformal metal containing films on substrates, such as: silicon, metal nitride, metal oxide and other metal-containing layers, using these metal-containing precursors.

Barium and strontium containing precursors are especially sought after for the deposition of thin barium and strontium oxide containing thin films, such as: barium strontium titanate oxide (BST) for advanced memory device manufacture. Although there are fluorinated barium precursors which have excellent volatility (ref), their use for BST manufacturing is effectively precluded, since fluoride ion can form in the oxide film and act as a charge carrier, which degrades the dielectric constant of the oxide film.

Thus, there is a strong need for unfluorinated barium and strontium precursor compounds, but such compounds are scarce, especially so for barium. This stems from the large ionic radius of the barium$^{+2}$ ion requiring ionic ligands which can provide a coordinating environment sufficient to provide compounds, which are monomeric or dimeric in barium. If this requirement is not met, the barium compounds tends to form highly associated or polymeric structures of limited volatility. However, even if monomeric or dimeric structures can be achieved, they may still not possess the thermal stability required to survive the high sublimation or distillation temperatures required for their vaporization. For all of these reasons, unfluorinated barium precursors, which are monomeric or dimeric, thermally stable, readily volatile and highly suited to BST manufacture by ALD or CVD, are extremely scarce, but highly sought after.

The prior art has attempted to provide precursors for these applications. However, none of the metal complexes in the prior art share the special characteristic of the complexes disclosed in the present invention. The compounds disclosed herein are exceptional in their volatility and thermal stability under conditions of vaporization. This makes them highly effective as precursors for BST film growth and any other application which requires volatile sources of barium. Similarly, these same ligand systems can also be applied to make volatile strontium, magnesium, radium or calcium precursors.

Related prior art to the present invention includes:

Harder, S. (2002); "Homoleptic beta Diketiminate Complexes of the Alkaline Earth Metals: Trends in the Series Mg, Ca, Sr, and Ba"; Organometallics 21(18), 3782-3787.

U.S. Pat. No. 5,319,118

El-Kaderi, H. M. and M. J. W. Heeg, C. H.; (2004). "Sandwich Complexes of the Heavier Alkaline Earth Metals Containing 5-Diketiminato Ligand Sets." Organometallics 23: 4995-5002.

M. J. Saly, M. J. Heeg and C. Winters, Inorganic Chemistry, publication date (Web) Apr. 27, 2009.

B. Sedai, M. J. Heeg and C. Winter, Organometallics, 2009, 18 (4) p 1032-1038.

Timo Hatanpaa, Marko Vehkamaki, Ilpo Mutikainen, Jarno Kansikas and Mikko Ritala "Synthesis and characterization of cyclopentadienyl complexes of barium: precursors for atomic layer deposition of BaTiO$_3$" Dalton Trans., 2004, 11811188.

H. Schmann, J. Gottfriedsen and J. Demtschuk "Synthesis and structure of eta-5 pyrrolyl complexes of calcium and strontium" Chem. Commun., 2091-2092, 1999).

WO 2009/086263A1.

BRIEF SUMMARY OF THE INVENTION

The present invention is a compound comprising a polyfunctionalized pyrrolyl anion and a second anion coordinated to at least one metal selected from the group consisting of barium, strontium or magnesium, radium, calcium and mixtures thereof, where the second anion is selected from the group consisting of polyfunctionalized pyrrolyl anion, beta-diketonates, acetates, ketoiminates, diimines, alkoxides, amides, hydrides, beta-ketoesters, amidinates, guanidinates, cyclopentadienyl, imidazolate, cyanide, isocyanide, formate, oxalate, malonate, phenoxide, thiolate, sulfide, nitrate, alkyl, silylalkyl, fluoroalkyl, aryl, imidazolate, hydride and mixtures thereof; except when there is only one metal and the first and second anion are polyfunctionalized pyrrolyl, then groups making the pyrrol polyfunctionalized are individually selected from the group consisting of acyl, formyl, nitro, amido, alkylamine, $C_1$-$C_{10}$ alkyl functionalized with a heteroatom substituted ring structure, such as: imidazole, pyrrole, pyridine, furan, pyrimidine, pyrazole, pyrrole, $C_1$-$C_{10}$ alkyl functionalized with an amide group, and $C_1$-$C_{10}$ alkyl functionalized with an ester group.

More preferably, the present invention is a compound selected from the group consisting of

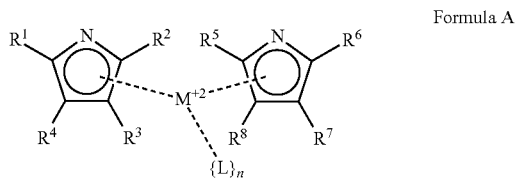

Formula A where $R^1$-$R^8$ are each individually acyl; formyl; amide, nitro; alkylamine; $C_1$-$C_{10}$ alkyl functionalized with a heteroatom substituted ring structure selected from the group consisting of imidazole, pyrrole, pyridine, furan, pyrimidine, pyrazole; $C_1$-$C_{10}$ alkyl functionalized with an amide group; $C_1$-$C_{10}$ alkyl functionalized with an ester group and mixtures thereof; wherein (L) is a neutral ligand selected from the group consisting of aliphatic $C_1$-$C_{20}$ ether or polyether; crownether; amine; poly amine; amide; poly amide; ester; polyester; aromatic ether; aromatic ester; aromatic amide; aromatic amine; pyridine; imidazole; pyridine; pyrazine; furan; pyrrole and mixtures thereof and n=0-4; and M=Ba, Sr, Ca, Ra or Mg; and, Formula B

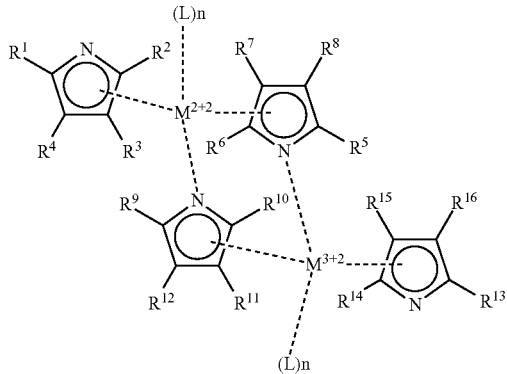

where $R^1$-$R^{16}$ are each individually acyl; formyl; amido, nitro; H; $C_1$-$C_{10}$ primary, seconday or tertiary alkyl; $C_1$-$C_{10}$ alkoxy; alkylamine; $C_1$-$C_{10}$ alkyl functionalized with a heteroatom substituted ring structure selected from the group consisting of imidazole, pyrrole, pyridine, furan, pyrimidine, pyrazole; $C_1$-$C_{10}$ alkyl functionalized with an amide group; $C_1$-$C_{10}$ alkyl functionalized with an ester group and mixtures thereof; wherein (L) is a neutral ligand individually selected from the group consisting of aliphatic $C_1$-$C_{20}$ ether or polyether; crownether; amine; poly amine; amide; poly amide; ester; polyester; aromatic ether; aromatic ester; aromatic amide; aromatic amine; pyridine; imidazole; pyridine; pyrazine; furan; pyrrole and mixtures thereof; $M^2$ and $M^3$ are individually selected from the group consisting of Ba, Sr, Ca, Ra or Mg; and each n independently=0-4.

Synthesis of the novel compounds and their use to form BST films is also contemplated.

In a further embodiment, there is provided a method for forming a metal-containing film on at least one surface of a substrate comprising the steps of: providing the at least one surface of the substrate; and forming the metal-containing film on the at least one surface by a deposition process chosen from a chemical vapor deposition process or an atomic layer deposition process from an at least one metal precursor within the Group 2 family (barium, strontium, magnesium, radium and calcium) with the structures described in formula A or B. The precursor can be co-reacted on a substrate surface to form a multi-element metal oxide film with another strontium complex, barium complex and/or titanium complex. The form of the additional precursors used in this co-reaction can be chosen from the cyclopentadienyl, diketonates, ketoesters, ketominates, guanidinates, amidates but are not limited to these families.

DETAILED DESCRIPTION OF THE INVENTION

The novel compounds of the present invention comprise anionic poly functionalized pyrrolyl ligands, which are coordinated to barium or strontium or magnesium, radium or calcium ions to yield either monomeric or dimeric compounds, in addition to neutral ligand adducts of those compounds, which have exceptional thermal stability and clean evaporation characteristics. For the purpose of the present invention, poly functionalized means that the pyrrolyl ring has groups bound to various of its carbons in substitution of the hydrogen that would otherwise be bound to the carbon. The substituting groups are identified and listed in this specification as the definitions of $R^1$-$R^{16}$.

The pyrrolyl rings can also be asymmetrically poly functionalized to yield lower melting point compounds of high solubility well suited to direct liquid injection (DLI). The structures of seven compounds in this series are shown in FIGS. 1, 2, 3, 4, (which can be dimerized to compounds of the present invention) and FIGS. 5, 6 and 7 (dimers for the present invention), where it can be seen that the compounds of FIGS. 1, 2, 3 and 4 (Formula A) are monomers and the compounds of FIGS. 5, 6 and 7 (Formula B) are dimers.

Figure 5:
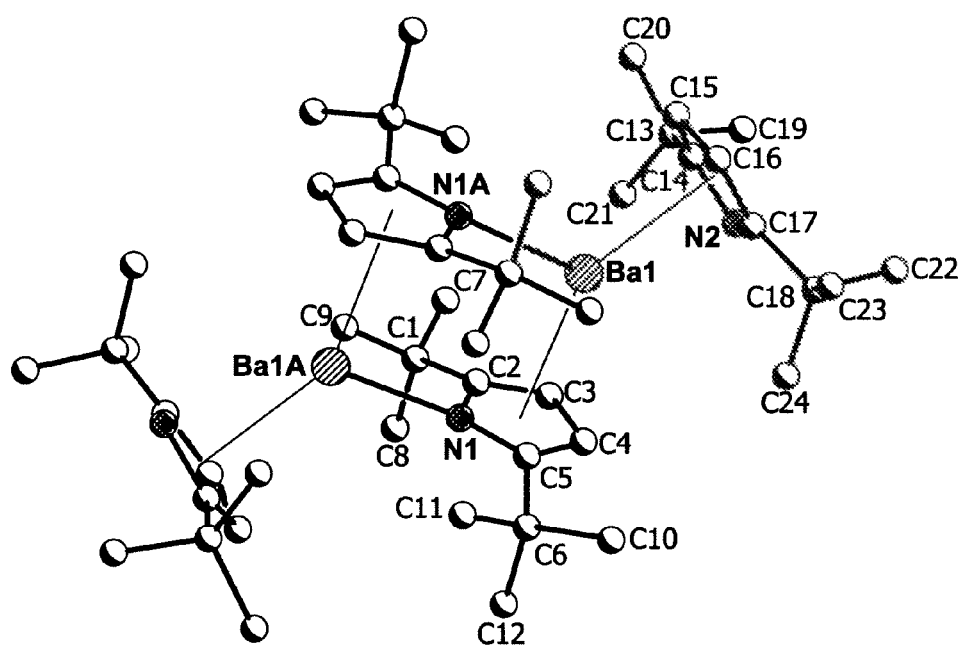
FIG. 5 illustrates di-barium tetrakis(2,5-di-tert-butylpyrrolyl) of Formula B as a dimer, no hydrogen atoms are shown.
Figure 6:
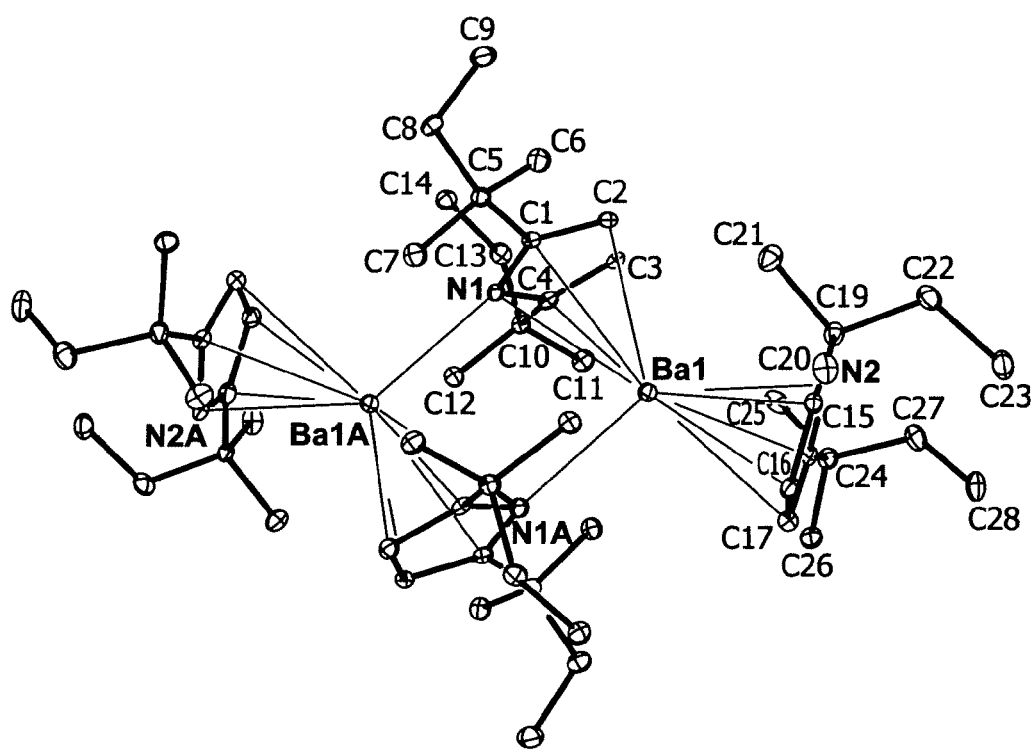
FIG. 6. illustrates di-barium tetrakis(2,5-di-tert-amylpyrrolyl) of Formula B, no hydrogen atoms are shown FIG. 7. illustrates di-strontium tetrakis(2,5-di-tert-amylpyrrolyl) of Formula B, no hydrogen atoms are shown
Figure 7:
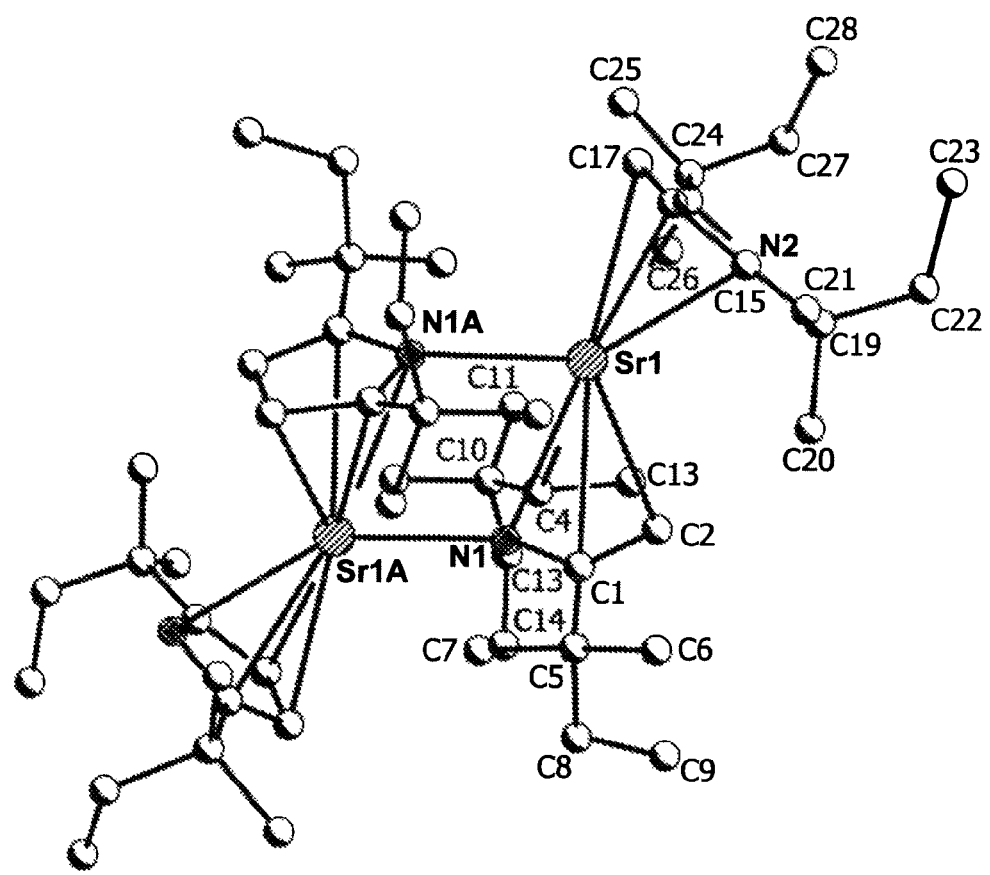
Figure 8:
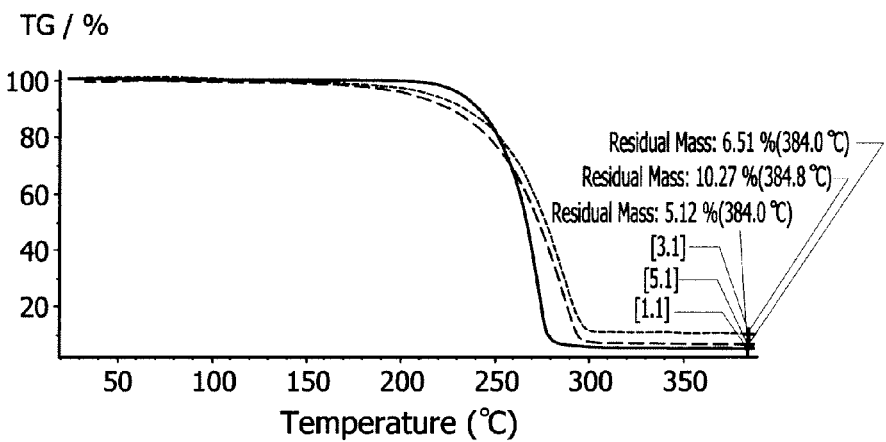
FIG. 8 shows a thermogravimetric analysis (TGA) comparison of presublimed barium bis(1,2,4-tri-tert-butylycyclopentadienyl) ie Ba(tBu$_3$Cp)$_2$ (dotted line), barium bis(2,3,5-tri-tert-butylpyrrolyl) (dashed line), and di-barium tetrakis(2,5-di-tert-butylpyrrolyl) (solid line).
Figure 9:
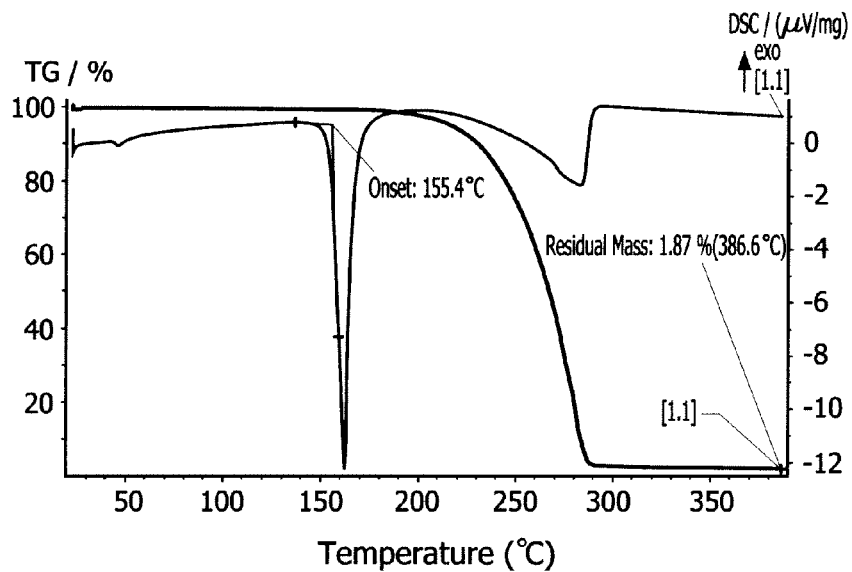
FIG. 9 shows a thermogravimetric analysis (TGA) comparison of presublimed di-strontium-tetrakis(2,5-di-tert-amylpyrrolyl)

When compared to state of the art alkaline earth precursors, the new compounds of FIGS. 5, 6 and 7 (Formula B) outperform them by leaving behind exceptionally low levels of involatile residues after exhaustive evaporation, as illustrated by the TGA runs in FIGS. 8 and 9.

One of the most well known family of barium compounds for ALD and CVD applications are the 'barocene' compounds, where the barium ion is coordinated to two multi alkyl functionalized cyclopentadienyl anions, such as tri-tert-butylcyclopentadienyl (t-Bu$_3$Cp). The synthesis and thermal properties of a series of nine different barium cyclopentadienyls are reported by Hatanpaa, et. al., listed in the Background section of this specification. In this study, as part of the full disclosure, Thermo Gravimetric Analysis (TGA) was used to screen the volatility/thermal stability of these compounds. In this technique, a sample of the barium compound is placed in a microbalance pan, which is heated at a steadily increasing rate under a steady stream of dry inert gas, such as nitrogen. As the temperature of the sample increases, the barium compound evaporates at an ever increasing rate, and this weight loss is detected by the microbalance. Eventually, the evaporation ceases, and, for barium, there is typically a residue of involatile material.

Using this approach, the highest performing specie was found to be Ba[t-Bu$_3$C$_5$H$_2$]$_2$, as its tetrahydrofuran (THF) adduct, as determined by its TGA residue being the lowest in the series. However, during the TGA process, the coordinated THF disassociates from the barium compounds, leaving the unsolvated barium compound to subsequently evaporate. Therefore, it is also informative to study the TGA performance of the unsolvated (THF free) barium complex.

We have performed this test and found an involatile residue of 10.3 wt % using a sample of this barium compound already purified by vacuum sublimation to remove THF and any other trace volatiles. When we tested barium compounds barium bis(2,3,5-tri-tert-butylpyrrolyl) (FIG. 3) and the present invention's di-barium tetrakis(2,5-di-tert-butylpyrrolyl) (FIG. 5) under identical TGA conditions, we found only 6.50 wt % and 5.12 wt % residues, respectively, indicating the new molecule to have superior evaporation and thermal stability charteristics. The results of all three TGA tests are summarized and illustrated in FIG. 8. It is noteworthy that all of the TGA data reported in Hatanpaa, et al., was run at atmospheric pressure versus under dynamic vacuum, since the latter represents a less demanding test of volatility and thermal stability. In other words, a substance, which can be sublimed cleanly under dynamic vacuum, may not sublime as cleanly under atmospheric pressure, since higher sublimation temperatures are required, and at these higher temperatures, the substance may be thermally unstable, and hence, begin to decompose, leaving a high level of involatile residue.

A low level of residue is highly desirable, as this translates to a controlled evaporation of the barium being possible, if it is used as a source precursor compound for ALD or CVD processes. In addition, for CVD or ALD processes, many metal precursors, such as barium precursors, are dissolved in a solvent, and this solution is vaporized in a DLI system. Basically, this comprises delivering a precisely controlled flow of solution into a vaporizer, where the solution and its dissolved solute are rapidly heated and vaporized under reduced pressure. The resulting vapor is then transported into the CVD or ALD reactor. Typically, there are minaturized nozzles and narrow bore tubes used inside the vaporizer at the point where the solution is nebulized or simply introduced into the vaporization temperature. If the solute does not fully evaporate and an involatile residue is formed, these fine bore tubes can become obstructed, thereby preventing any further flow of solution. For these reasons, it is highly desirable for the involatile residue observed in the TGA experiment to be as low as possible to avoid the accumulation of obstructing residues for the best possible DLI performance. This is especially important in a commercial manufacturing environment, where such an equipment failure is prohibitively expensive.

The present invention is directed to the synthesis and use of new and novel barium, strontium, magnesium, radium and calcium poly functionalized pyrrolyl-based compounds and their solutions for vapor delivery upon direct liquid injection, wherein the functionalizing groups of the pyrrolyl ligand anion can be bulky hydrocarbons, such as: tert-butyl, tert-amyl, etc.; and can be nitrogen or oxygen containing alkyl, such as: tertiary amine or ether groups for the dimers of the present invention and nitrogen and tertiary amine for the monomers. Additionally, these new compounds can also coordinate other neutral ligands, such as: ethers or amines or alkoxyamines. Electron withdrawing groups, such as nitro, can also be present as a pyrrole ring substituent.

While not wishing to be bound by theory, groups, such as nitro, enhance the effective binding of added neutral ligands, such as: THF, diglyme, 18-crown-6 crown ether, by rendering the pyrrolyl anion less electron donating to barium or strontium or other alkaline earth metal, and hence, increase the Lewis acididty of the metal towards added ligands, and hence, increase their affinity (binding constant) to the metal. Achieving this higher binding permits the entire barium or strontium compound, with coordinated ligands, such as THF, to vaporize intact as one complete compound, rather than releasing this coordinated ligand first.

The present invention also includes a novel method of synthesizing the barium, strontium, magnesium, radium or calcium compounds by direct metallization of the pyrrole ligands using a metal reagent, such as barium or strontium hexamethyldisilazane or barium hydride, thereby providing an efficient alternative to using the standard metathesis type of reaction, where the pyrrole is first treated with a metal hydride, such as sodium hydride, to form a sodium pyrrolide, which is then in turn reacted with a barium or strontium halide, such as barium or strontium iodide etc.

Other novel techniques for synthesizing these new compounds include, but are not limited to, direct reaction of the pyrrole ligands with barium, strontium, magnesium or calcium metal or by reaction with barium or strontium metal, etc., in the presence of ammonia or by reacting the pyrrole ligands with barium metal in the presence of an amine, such as hexamethyldisilazane, with ammonia. The novel compounds may also be prepared by electochemical syntheses.

Additionally, a wide variety of metals and metalizing agents can be used to effectively deprotonate the pyrrole ligands prior to reacting with a barium, strontium, magnesium, radium or calcium source. Such reagents include, but are not limited to: n-butyl lithium, n-hexyl lithium, sec-butyl lithium, tert-butyl lithium, lithium diisopropylamide, potassium hydride, sodium hydride, sodium metal, potassium metal, barium metal, sodium t-butoxide, potassium t-butoxide. Barium sources include, but are not limited to: barium iodide, barium bromide, barium trifluoroacetate, barium hexafluoroacetylacetone, barium trifluoroacetylacetonate, barium acetyacetonate, barium diimine, barium ketoimine, barium amidinate, barium guanidinate, barium amide, barium alkoxide, barium amide, barium carbonate, barium acetate, barium carbonate, barium formate, barium propionate, barium phenoxide, barium hydroxide and the strontium, magnesium, radium and calcium analogs to the barium sources.

The novel poly functionalized pyrrole barium, magnesium, calcium, radium or strontium compounds of the present invention are selected from the following structures in: (i)

Formula A, where $R^1$-$R^8$ are each individually selected to be acyl, formyl, nitro, amido, alkylamine, $C_1$-$C_{10}$ alkyl functionalized with a heteroatom substituted ring structure, such as: imidazole, pyrrole, pyridine, furan, pyrimidine, pyrazole, pyrrole, $C_1$-$C_{10}$ alkyl functionalized with an amide group, and $C_1$-$C_{10}$ alkyl functionalized with an ester group; and each n independently=0-4, preferably each n independently=0, 1 or 2; and, (ii) Formula B, where $R^1$-$R^{16}$ are each individually selected to be acyl, formyl, nitro, amido, H, $C_1$-$C_{10}$, primary, seconday or tertiary alkyl, $C_1$-$C_{10}$ alkoxy, alkylamine, $C_1$-$C_{10}$ alkyl functionalized with a heteroatom substituted ring structure, such as: imidazole, pyrrole, pyridine, furan, pyrimidine, pyrazole, pyrrole, $C_1$-$C_{10}$ alkyl functionalized with an amide group, and $C_1$-$C_{10}$ alkyl functionalized with an ester group; and each n independently=0-4, preferably each n independently=0, 1 or 2. Note that neutral ligand-free molecules, where n=zero in $(L)_n$ to indicate that there is no (L) ligand coordinated, are also described. Note that neutral ligand-free molecules, where n=zero in $(L)_n$ to indicate that there is no (L) ligand coordinated, are also described.

Mixed complexes can also be created where $R^{1-16}$ are varied differently among pyrrolyl anions, and then this mixture is complexed to barium, or other alkaline earth metal so that the resulting metal complex represents a mixture. Thus, if two different pyrroly anions $P^1$ and $P^2$ are mixed together, and then complexed to, for example, barium, three unique barium complexes can be made; i.e., $Ba(P^1)_2$, $Ba(P^1P^2)$ and $Ba(P^2)_2$. If three different pyrrolyl anions $P^1$, $P^2$ and $P^3$ are mixed, and then complexed to barium, six barium complexes are formed; i.e., $Ba(P^1)_2$, $Ba(P^1P^2)$, $Ba(P^1P^3)$, $Ba(P^2)_2$, $Ba(P^2P^3)$ and $Ba(P^3)_2$. In these examples, other alkaline earth metals are also contemplated and the pyrrols "P" can be functionalized as described elsewhere in this specification.

These mixtures will be either liquids or highly soluble for DLI formulations. In all of these compounds, the pyrrolyl anions can coordinate in an eta-5 mode, where each atom of the 5-membered pyrrole ring is bonded to the metal; or an in eta-4 mode, where four of the pyrrole ring atoms bond to the metal; or in an eta-3 mode, where three of the pyrrole ring atoms bond to the metal; or in an eta-2 mode, where two of the pyrrole ring atoms bond to the metal; or in an eta-1 mode, where only one atom of the pyrrole ring bonds to the metal. Additionally, the pyrrole rings can also bond to the metal in a mixed mode, such as eta-1 and eta 5, which is shown in FIGS. 5, 6 and 7. The groups R of one pyrrolyl anion can also be joined to the R groups of another pyrrolyl anion to connect the two anions together.

The neutral ligand (L) in Formula A and Formula B, below, is selected from aliphatic $C_1$-$C_{20}$ ether or polyether, crownethers, such as 18-crown-6, amine or polyamine, alkoxyamine or polyalkoxyamine, amide or polyamide, ester or polyester, aromatic ether, aromatic ester, aromatic amide, aromatic amine, pyridine, imidazole, pyridine, pyrazine, furan, alkylcarbonate or pyrrole.

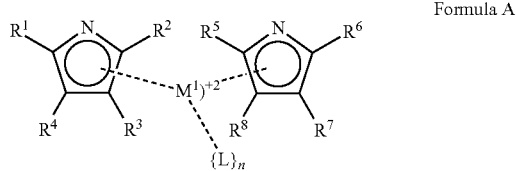

Formula A

Formula A represents compounds of the present invention, where $R^1$, $R^2$, $R^3$, $R^4$, $R^5$, $R^6$, $R^7$, $R^8$ are each individually selected to be acyl, formyl, nitro, amido, alkylamine, $C_1$-$C_{10}$ alkyl functionalized with a heteroatom substituted ring structure, such as: imidazole, pyrrole, pyridine, furan, pyrimidine, pyrazole, pyrrole, $C_1$-$C_{10}$ alkyl functionalized with an amide group, and $C_1$-$C_{10}$ alkyl functionalized with an ester group; and each n independently=0-4, preferably each n independently=0, 1 or 2; and M is barium, magnesium, calcium, radium or strontium. Additionally, one or more of groups $R^1$, $R^2$, $R^3$ and $R^4$ and one or more of groups $R^5$, $R^6$, $R^7$ and $R^8$ can be linked together to form ring structures, These ring structures can also be aromatic.

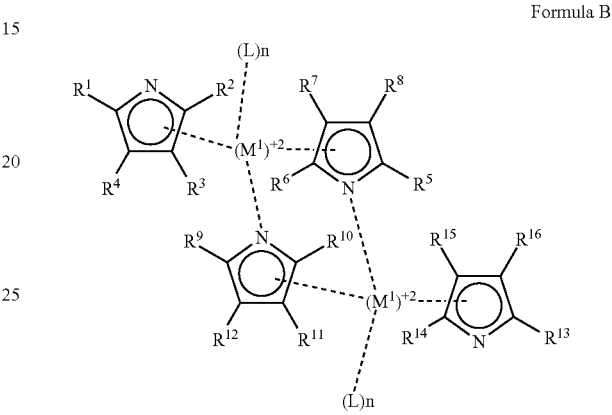

Formula B

Formula B represents additional compounds of the present invention, where $R^1$-$R^{16}$ are each individually selected to be acyl, formyl, nitro, amido, H, $C_1$-$C_{10}$, primary, seconday or tertiary alkyl, $C_1$-$C_{10}$ alkoxy, alkylamine, $C_1$-$C_{10}$ alkyl functionalized with a heteroatom substituted ring structure, such as: imidazole, pyrrole, pyridine, furan, pyrimidine, pyrazole, pyrrole, $C_1$-$C_{10}$ alkyl functionalized with an amide group, and $C_1$-$C_{10}$ alkyl functionalized with an ester group; and each n independently=0-4, preferably each n independently=0, 1 or 2; and $M^1$ is selected from the group consisting of barium, magnesium, calcium, radium and strontium. The neutral ligands are as set forth above. One or more of the R groups of one pyrrole can be bonded to one or more R groups of another pyrrole in Formula B, as was stated above for Formula A.

In Formulae A and B, $M^1$ is a Group 2 metal selected from: magnesium, calcium, strontium, barium, radium, preferably strontium and barium, more preferably barium. In instances where the presence of fluorine in the precursors does not present a problem, $R^{1-16}$ can also be fluoroalky, fluoroalkoxy or fluoroarylalkyl. In instances where the presence of the element silicon does not pose any issues, $R^{1-16}$ can be trialkylsilyl. Similarly, species where $R^{1-16}$ are individually selected from alky, fluoroalkyl and trialkylsilyl can be prepared.

Additionally, new compounds of the type in Formula C are described, which are of the same family as Formula B, but contain two different metals $(M^2)$ and $(M^3)$ where $M^2$ and $M^3$ are chosen from divalent metals, such as: Be, Mg, Ca, Sr, Ba, or Ra.

Formula C

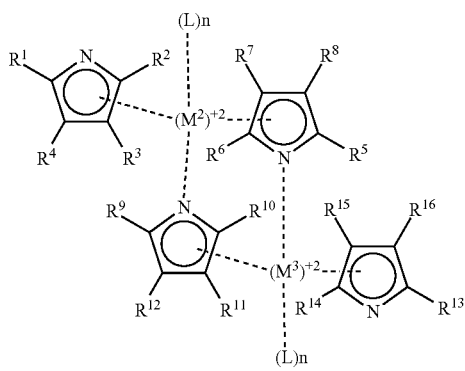

In addition to the above complexes, while not wishing to be bound by theory, mixed barium complexes can also be made where one poly functionalized pyrrolyl anion and one other organic or inorganic anion coordinate to barium or other alkaline earth metals to make a complete complex. Examples of such alternative anions include, but are not limited to, beta-diketonates, acetates, ketoiminates, diimines, alkoxides, amides, hydrides, beta-ketoesters, amidinates, guanidinates, cyclopentadienyl, cyanide, isocyanide, formate, oxalate, malonate, phenoxide, thiolate, sulfide, nitrate, alkyl, silylalkyl, fluoroalkyl, aryl, imidazolate. Other alkaline earth metal complexes, as described above, are also contemplated.

Several advantages can be achieved through these metal-containing polyalkylated pyrroles as precursors for chemical vapor deposition or atomic layer deposition, and these include:

an ability to form reactive complexes in good yield;
an ability to form monomeric thermally stable complexes, particularly strontium and barium complexes, coordinated with one kind or mixed kind of ligand, thus achieving higher vapor pressure than that of the known strontium and barium precursors. The known strontium and barium precursors are either polymeric complexes with lower vapor pressure or monomeric compounds with Low thermal stability or with relatively high levels of involatile residues;
an ability to form highly conformal metal oxide thin films suited for use in microelectronic devices;
an ability to enhance the surface reaction between the metal-containing alkylated pyrrolyl anion and the surface of a substrate due to the high chemical reactivity of the complexes; and,
an ability to tune the physical properties of these metal-containing polyalkyl pyrrolylanions via a change in the $R^{1-4}$ groups.

Additionally, metal complexes can also be made by coordinating two different poly functionalized pyrrolyl anions to a metal center, such as barium, such that the two ligands experience an optimal 'fit' or 'interlock' with each other and around the metal in such a way as to provide an adequate coordination sphere to create a stable monomeric complex.

While not wishing to be bound by theory, the molecules of this disclosure are excellent precursors for use in CVD or ALD processes for depositing alkaline earth metal oxide containing films, by reacting them together either sequentially or simultaneously with an oxidizer, such as: water, alcohol, oxygen, ozone, nitrous oxide, nitrogen dioxide, hydrogen peroxide or combinations thereof. Additionally, barium and strontium molecules of this disclosure can be reacted with a titanium precursor, such as: a titanium alkoxy/diketonate, titanium alkoxide, titanium cyclopentadienyl, titanium amide, titanium ketoesters, titanium halide, titanium nitrate, or combinations thereof, in a CVD, pulsed CVD or ALD mode to deposit BST (barium strontium titanate) films, STO (strontium titanate) and BTO (barium titanate) which are highly prized, due to their high dielectric constant. Additionally, the barium complexes of this disclosure can be reacted with strontium ketoiminates and titanium precursors, such as: a titanium alkoxy/diketonate, titanium alkoxide, titanium cyclopentdienyl, titanium amide or combinations thereof, in a CVD, pulsed CVD or ALD mode to deposit a BST film.

The method disclosed herein deposits the Group 2 metal containing films using atomic layer deposition (ALD) or chemical vapor deposition (CVD) processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via plasma enhanced ALD (PEALD) or plasma enhanced cyclic CVD (PECCVD) process. In these embodiments, the deposition temperature may be relatively lower, or may range from 200° C. to 400° C., and may allow for a wider process window to control the specifications of film properties required in end-use applications. Exemplary deposition temperatures for the PEALD or PEC-CVD deposition include ranges having any one or more of the following endpoints: 200, 225, 250, 275, 300, 325, 350, 375, and/or 400° C.

As mentioned previously, the method disclosed herein forms the metal-containing films using at least one metal precursor such as the Group 2 metal-containing precursors having formulae described herein, optionally an oxygen source, optionally an additional metal-containing or other metal-containing precursor, optionally a reducing agent, and optionally a nitrogen source. Although the precursors and sources used herein may be sometimes described as "gaseous", it is understood that the precursors can be either liquid or solid which are transported with or without an inert gas and/or solvent into the reactor via direct vaporization, bubbling or sublimation. In some case, the vaporized precursors can pass through a plasma generator.

Substrates for the deposition method can include silicon oxide, an electrode surface such as ruthenium, platinum, titanium nitride, tantalum nitride or other substrates common in semiconductor devices.

In certain embodiments, other metal-containing precursors can be used in addition to the Group 2 metal-containing precursors described herein. Metals commonly used in semiconductor fabrication include that can be used as the metal component for the metal amide includes: titanium, tantalum, tungsten, hafnium, zirconium, cerium, zinc, thorium, bismuth, lanthanum, strontium, barium, lead, and combinations thereof. Examples of other metal-containing precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino) hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino) tantalum (TBTDET), tert-butylimino tri(dimethylamino) tantalum (TBTDMT), tert-butylimino tri(ethylmethylamino) tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, bis(2,2,6,6-tetramethyl-3,5-heptanedionato)strontium, bis(2,2,6,6-tetramethyl-3,5-heptanedionato)barium, $M(R_mC_{5-m-n}H_n$ wherein M=Sr or Ba, n is a integer from 1 to 4, n+m=5, and combinations thereof.

As previously mentioned, some of the films deposited using the methods described herein may be formed in the presence of oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In this or other embodiments wherein the film is deposited by an ALD process, the precursor pulse can have a pulse duration that is greater than 0.01 seconds, and the oxidant pulse duration can have a pulse duration that is greater than 0.01 seconds, while the water pulse duration can have a pulse duration that is greater than 0.01 seconds. In yet another embodiment, the purge duration between the pulses that can be as low as 0 seconds.

The deposition methods disclosed herein may involve one or more purge gases. The purge gas, which is used to purge away unconsumed reactants and/or reaction byproducts, is an inert gas that does not react with the precursors and may preferably be selected from the group consisting of Ar, $N_2$, He, $H_2$ and mixture thereof. In certain embodiments, a purge gas such as Ar is supplied into the reactor at a flow rate ranging from about 10 to about 2000 sccm for about 0.1 to 1000 seconds, thereby purging the unreacted material and any byproduct that remain in the reactor.

In certain embodiments, an additional gas such as a nitrogen source gas may be introduced into the reactor. Examples of nitrogen source gases may include, for example, NO, $NO_2$, ammonia, hydrazine, monoalkylhydrazine, dialkylhydrazine, and combinations thereof.

In one embodiment of the method described herein, the temperature of the substrate in the reactor, i.e., a deposition chamber, is about 600° C. or below or about 500° C. or below or from 250 to 400° C. In this or other embodiments, the pressure may range from about 0.1 Torr to about 100 Torr or from about 0.1 Torr to about 5 Torr.

The respective step of supplying the precursors, the oxygen source, and/or other precursors or source gases may be performed by changing the time for supplying them to change the stoichiometric composition of the resulting metal-containing film.

Energy is applied to the at least one of the precursor, oxygen source gas, reducing agent, or combination thereof to induce reaction and to form the metal-containing film on the substrate. Such energy can be provided by, but not limited to, thermal, plasma, pulsed plasma, helicon plasma, high density plasma, inductively coupled plasma, X-ray, e-beam, photon, and remote plasma methods. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

In yet another embodiment of the method disclosed herein, the Group 2 metal-containing film is formed using a vapor deposition method that comprises the steps of: (a) introducing a Group 2 metal-containing precursor in a vapor state into a reaction chamber and chemisorbing the metal-containing precursor onto a substrate which is heated; (b) purging away the unreacted Group 2 metal-containing precursor; (c) introducing an oxygen source onto the heated substrate to react with the sorbed Group 2 metal-containing precursor; and (d) purging away the unreacted oxygen source. The above steps define one cycle for the method described herein; and the cycle can be repeated until the desired thickness of a metal-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and the oxygen source gases may be performed by varying the duration of the time for supplying them to change the stoichiometric composition of the resulting metal oxide film. For multicomponent metal oxide films, a strontium-containing precursor, a barium-containing precursor or both precursors can be alternately introduced in step (a) into the reactor chamber.

The Group 2 metal-containing precursor and/or other metal containing precursors may be delivered to the reaction chamber, such as a CVD or ALD reactor, in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Mn, to enable low volatility materials to be volumetrically delivered, leading to reproducible transport and deposition without thermal decomposition of the precursor. Both of these considerations of reproducible transport and deposition without thermal decomposition are essential for providing a commercially acceptable copper CVD or ALD process.

In one embodiment of the method described herein, a cyclic deposition process such as CCVD, ALD, or PEALD may be employed, wherein a Group 2 metal-containing precursor or its solution and an oxygen source such as, for example, ozone, oxygen plasma or water plasma are employed. The gas lines connecting from the precursor canisters to the reaction chamber are heated to one or more temperatures ranging from about 150° C. to about 200° C. depending upon the process requirements, and the container of the Group 2 metal-containing precursor is kept at one or more temperatures ranging from about 100° C. to about 190°

C. for bubbling whereas the solution comprising the Group 2 metal-containing precursor is injected into a vaporizer kept at one or more temperatures ranging from about 150° C. to about 180° C. for direct liquid injection. A flow of 100 sccm of argon gas may be employed as a carrier gas to help deliver the vapor of the Group 2 metal-containing precursor to the reaction chamber during the precursor pulsing. The reaction chamber process pressure is about 1 Torr. In a typical ALD or CCVD process, the substrate such as silicon oxide or metal nitride are heated on a heater stage in a reaction chamber that is exposed to the Group 2 metal-containing precursor initially to allow the complex to chemically adsorb onto the surface of the substrate. An inert gas, such as argon gas, purges away unadsorbed excess complex from the process chamber. After sufficient Ar purging, an oxygen source is introduced into reaction chamber to react with the absorbed surface followed by another inert gas purge to remove reaction by-products from the chamber. The process cycle can be repeated to achieve the desired film thickness.

In liquid delivery formulations, the precursors described herein may be employed in solvent formulations or compositions comprising same. Thus, in certain embodiments the precursor formulations may include solvent component(s) of suitable character as may be desirable and advantageous in a given end use application to form a film on a substrate. The solvent employed in solubilizing the precursor for use in a deposition process may comprise any compatible solvent or their mixture, including: aliphatic hydrocarbons (e.g., hexane, heptane, octane, and pentane), aromatic hydrocarbons (e.g., benzene or toluene), ethers, esters, nitriles, alcohols, amines (e.g., triethylamine, tert-butylamine), imines and carbodiimides (e.g., N,N'-diisopropylcarbodiimide), ketones, aldehydes, amidines, guanadines, isoureas, and the like. Further examples of suitable solvent are selected from the group consisting of glyme solvents having from 1 to 20 ethoxy —($C_2H_4O$)— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers, wherein the prefixed $C_i$ range is the number i of carbon atoms in the ether compound and the suffixed $O_j$ range is the number j of oxygen atoms in the ether compound; $C_6$-$C_{12}$ aliphatic hydrocarbons; $C_6$-$C_{18}$ aromatic hydrocarbons; organic esters; organic amines, polyamines, aminoethers and organic amides. Another class of solvents that offers advantages is the organic amide class of the form RCONR'R'' wherein R and R' are alkyl having from 1-10 carbon atoms and they can be connected to form a cyclic group $(CH_2)_n$, wherein n is from 4-6, preferably 5, and R'' is selected from alkyl having from 1 to 4 carbon atoms and cycloalkyl. N-methyl- or N-ethyl- or N-cyclohexyl-2-pyrrolidinones, N,N-Diethylacetamide, and N,N-Diethylformamide are examples.

Figure 10:
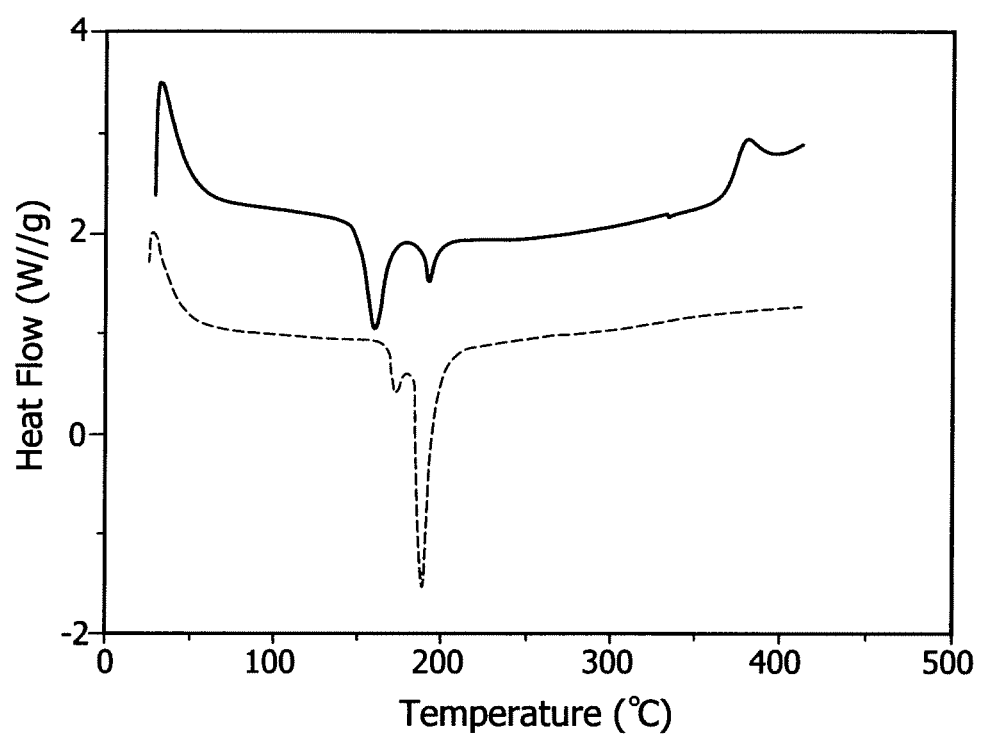
FIG. 10 shows a direct scanning calorimetry (DSC) comparison of barium bis(1,2,4-tri-tert-butylycyclopentadienyl) ie Ba(tBu$_3$Cp)$_2$ and di-barium tetrakis(2,5-di-tert-butylpyrrolyl).
Figure 11:
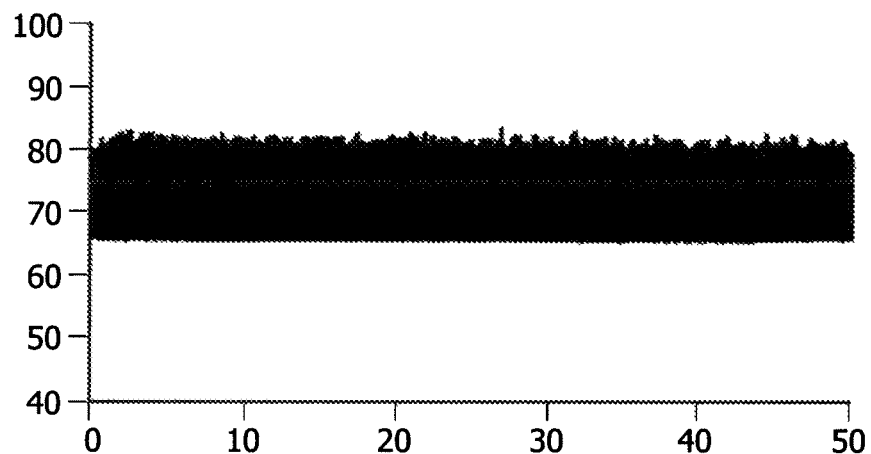
FIG. 11 shows an example of direct liquid injection of 0.05M di-barium tetrakis(2,5-di-tert-butylpyrrolyl) dissolved in solvent 2,2'-oxybis(N,N-dimethylethanamine). The graph is a plot of pressure stability as the precursor/solvent was pulsed into a heated delivery line via a heated vaporized. The test was performed over 50 hours of extended run to demonstrate the stability of the pulsing and delivery with this combination.

One specific embodiment for liquid delivery of these precursors is demonstrated in FIG. 10 where 0.05M di-barium tetrakis(2,5-di-tert-butylpyrrolyl) is dissolved in solvent 2,2'-oxybis(N,N-dimethylethanamine). The pressure stability over 50 hour run time demonstrates the stability of this formulation during continuous liquid delivery. This is especially advantageous for the semiconductor applications where continuous operation is critical for manufacturing. The boiling point of the solvent to the required vaporizer temperature is particularly well-matched for robust precursor delivery.

The utility of specific solvent compositions for particular precursors may be readily empirically determined, to select an appropriate single component or multiple component solvent medium for the liquid delivery vaporization and transport of the specific Group 2 precursor that is employed.

In another embodiment, a direct liquid delivery method can be employed by dissolving the Group 2 metal-containing precursor in a suitable solvent or a solvent mixture to prepare a solution with a molar concentration from 0.01 to 2 M, depending the solvent or mixed-solvents employed. The solvent employed herein may comprise any compatible solvents or their mixture including, but not limited to, aliphatic hydrocarbons, aromatic hydrocarbons, linear or cyclic ethers, esters, nitriles, alcohols, amines, polyamines, and organic amides, aminoethers preferably a solvent with a high boiling point.

The method described herein also includes a cyclic deposition process for the formation of ternary metal oxide films, wherein a plurality of precursors are sequentially introduced into a deposition chamber, vaporized and deposited on a substrate under conditions for forming a said ternary metal oxide film.

In one particular embodiment, the resultant metal oxide films can be exposed to a post-deposition treatment such as a plasma treatment to densify and/or crystallize the film.

The following examples illustrate the method for preparing a Group 2 metal-containing precursor described herein are not intended to limit it in any way.

EXAMPLES 2,5-di-tert-butylpyrrole, 2,3,5-tri-tert-butylpyrrole and barium hexamethyldisilazide were prepared according to literature procedures (R. Ramasseul and A. Rassat, Chemical Communications, 1965, 453; and B. A. Vaarstra, J. C. Huffman, W. E. Streib, K. G. Caution, Inorganic Chemistry, 30, 121-125, 1991, respectively). 3,3,6,6-tetramethyl-4,5-octanedione and 2,5-di-tert-amylpyrrole was synthesized according to examples 1 and 2, respectively, below.

Example 1

Synthesis of 3,3,6,6-tetramethyl-4,5-octanedione 2-chloro-2-methyl butane (48 mL, 0.39 mol) was slowly added to magnesium pellets (9.5 g, 0.39 mol) in 390 mL of THF to make the Grignard reagent, t-amylMgCl. This was added slowly to a mixture of cuprous chloride (12 g, 0.12 mol) and succinyl chloride (13.5 mL, 0.12 mol), cooled to −50° C. in dry ice. After addition, the mixture was allowed to warm up to room temperature overnight. Most of the THF is removed by vacuum, followed by the addition of 500 mL of hexanes and 200 mL of 2M HCl. This mixture was filtered to remove the solid byproducts. The aqueous layer was washed 3× with 100 mL of hexanes, the hexanes layer washed 3× with 200 mL of 2M HCl, 2× with 200 mL of $NaHCO_3$/water, 1× with 200 mL of water, and finally 1× with 200 mL of NaCl/water. The product mixture was then dried for an hour over 20 g of anhydrous magnesium sulfate, which was subsequently removed by filtration. The hexane was then removed by atmospheric distillation to yield 8.4 g (72%) of finished product, characterized by Mass Spectrometry: Parent ion at 227 m.u Example 2

Synthesis of 2,5-di-tert-amylpyrrole 33.6 g (0.146 mol) of 3,3,6,6-tetramethyl-4,5-octanedione, 22.51 g (0.292 moles) of ammonium acetate and 50.1 mL (0.0.876 moles) of acetic acid were refluxed to 140° C. overnight. The resulting product mixture was neutralized with sodium bicarbonate solution, then extracted with hexanes.

The aqueous layer was washed 3× with 100 mL of hexanes. The hexane layer was washed 3× with 100 mL of water then stood over 20 g of anhydrous magnesium sulfate for 2 hrs then removed by filtration. Hexanes was then removed by vacuum, yield 27.6 g (92%). Characterized by Mass Spectrometry: Parent ion at 207 m.u Example 3

Figure 1:
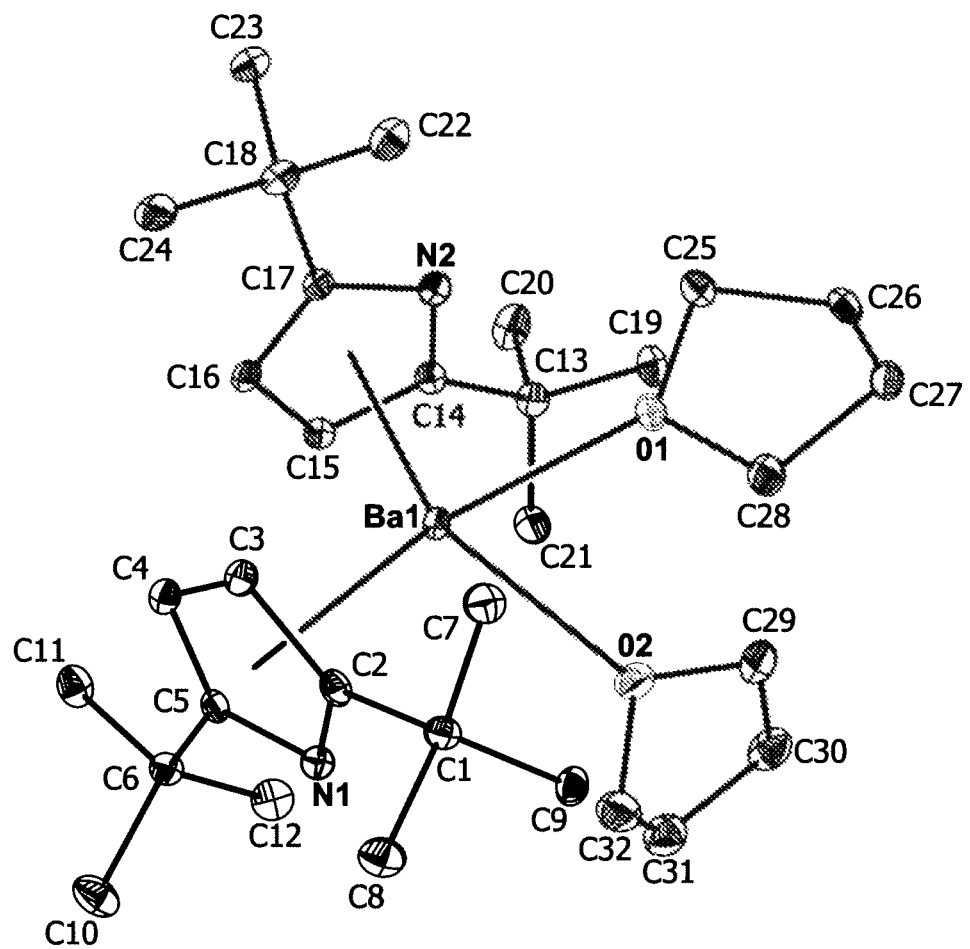
FIG. 1 illustrates barium bis(2,5-di-tert-butylpyrrolyl) bis tetrahydrofuran of Formula A as a monomer, no hydrogen atoms are shown.

Synthesis of barium bis(2,5-di-tert-butylpyrrolyl) bis tetrahydrofuran, i.e., Ba complex in FIG. 1 as an Example 7 precursor Under a nitrogen atmosphere, 1.98 g (0.011 moles) of 2,5-di-tert-butylpyrrole was dissolved with stirring in 25 ml of dry deoxygenated THF at room temperature. 3.34 g (0.0055 moles) of barium hexamethyldisilazide $(THF)_2$ dissolved in 10 ml THF were added over 10 minutes, and the mixture was allowed to stir overnight. The solvent and volatiles were then removed from this reaction mixture under vacuum and collected in a liquid nitrogen trap. Gas chromatograph mass spectroscopy (GCMS) analysis of the resulting liquid showed a high concentration of hexamethyldisilazane, indicating that the deprotonation of the pyrrole had proceeded as desired. The remaining off-white solid reaction mixture was then dissolved in 35 ml of boiling hexane, allowed to cool to room temperature, and then stood overnight in a −20° C. freezer. The hexane supernatant liquor was decanted off, and the resulting colorless crystals dried under vacuum to yield 2.5 g of product (71% yield based on 2,5-di-tert-butylpyrrole).
$^1$H NMR: (500 MHz, $C_6D_6$): δ=1.3 (m, 8H), δ=1.45 (s, 36H), δ=3.5 (m, 8H), δ=6.3 (s, 4H).

Example 4

Figure 2:
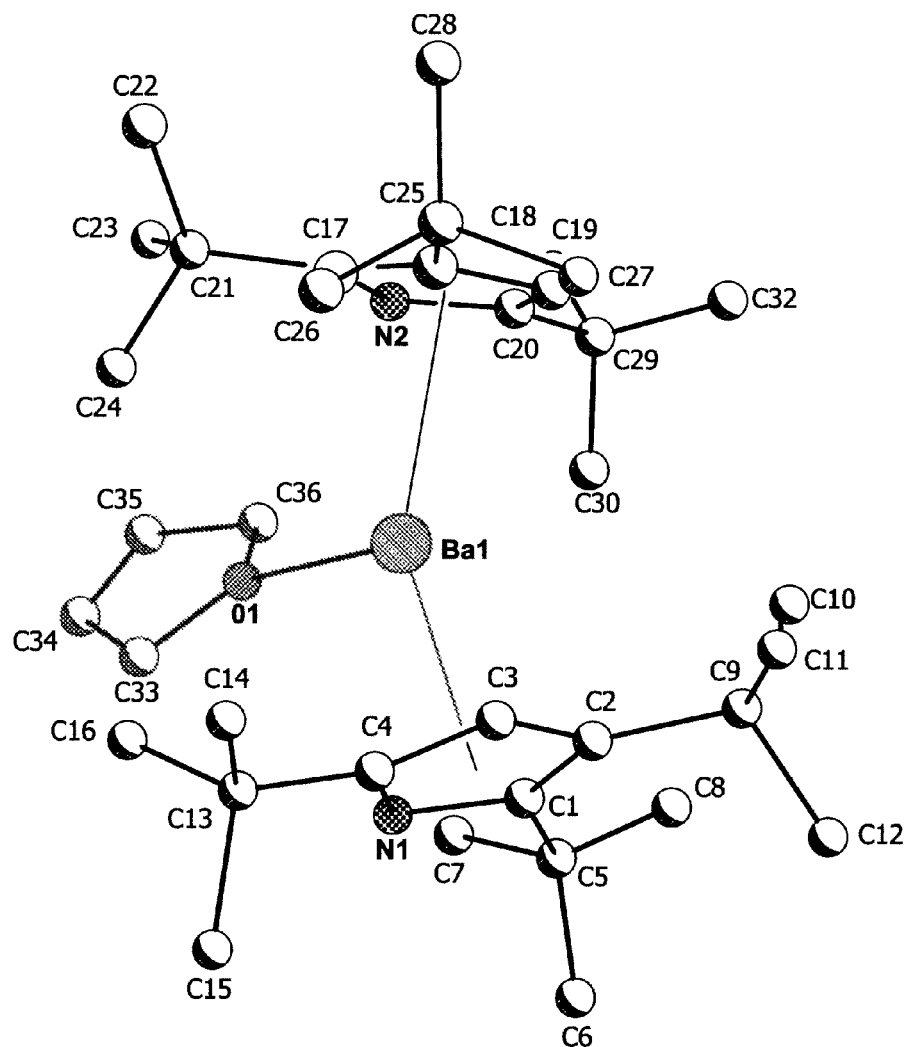
FIG. 2 illustrates barium bis(2,3,5-tri-tert-butylpyrrolyl) tetrahydrofuran of Formula A as a monomer, no hydrogen atoms are shown.

Synthesis of barium bis(2,3,5-tri-tert-butylpyrrolyl)(THF), i.e., Ba complex in FIG. 2

20 mg of barium bis(2,3,5-tri-tert-butylpyrrole) were dissolved in 0.1 ml of THF, and then the solvent was removed by evaporation. The resulting crystalline mass was then recrystallized in hexane to yield approximately 10 mg of crystals, which were then shown to be the desired product by X-ray analysis.

Example 5

Figure 3:
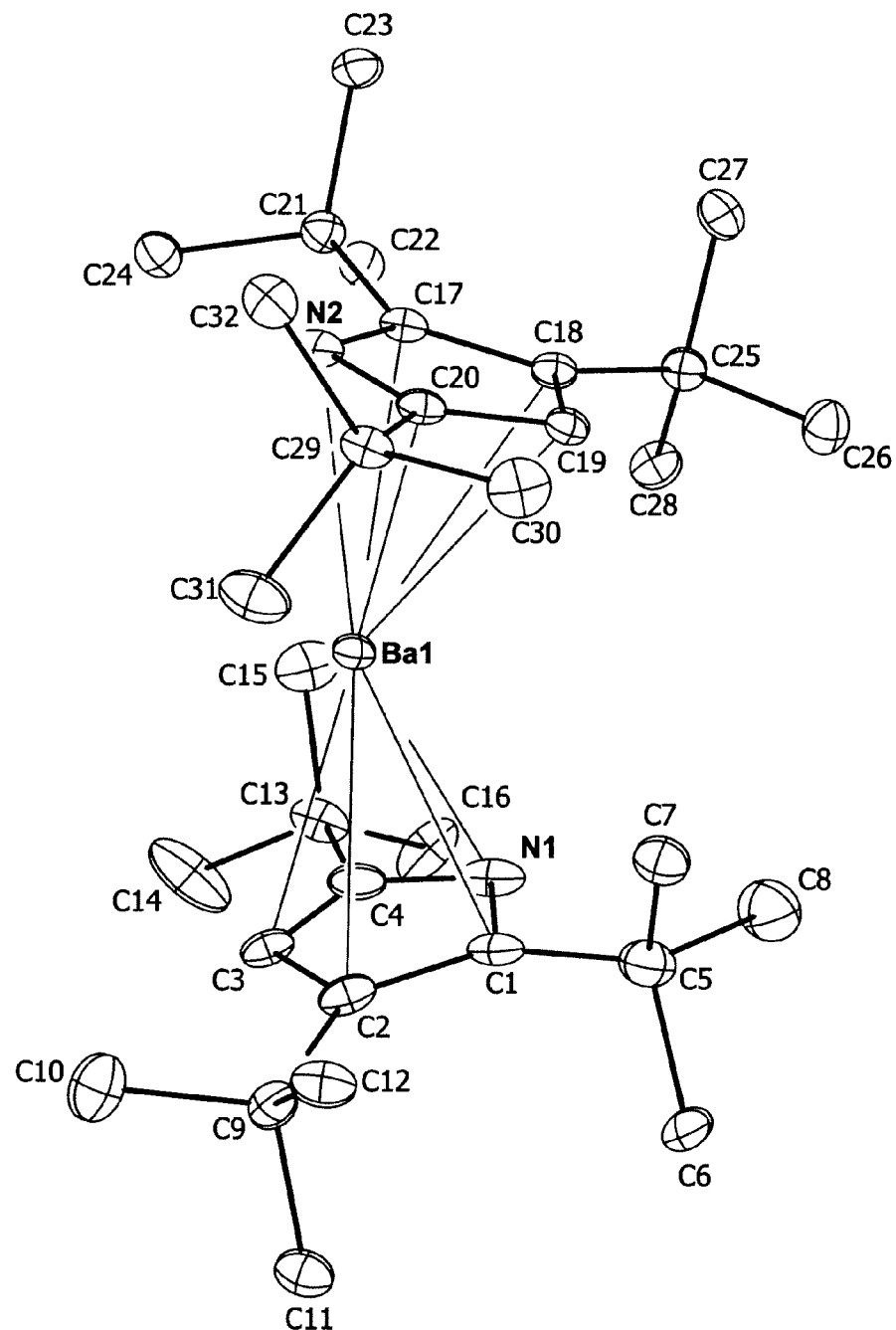
FIG. 3 illustrates barium bis(2,3,5-tri-tert-butylpyrrolyl) of Formula A) as a monomer, no hydrogen atoms are shown.

Synthesis of barium bis(2,3,5-tri-tert-butylpyrrolyl) in FIG. 3

Under a nitrogen atmosphere, 0.483 g (0.00205 moles) of 2,3,5-tri-tert-butylpyrrole was dissolved with stirring in 10 ml of dry deoxygenated THF at room temperature. 0.6 g (0.00102 moles) of barium hexamethyldisilazide $(THF)_2$ dissolved in 10 ml THF were added over 10 minutes and the mixture was allowed to stir overnight. The solvent and volatiles were then removed from this reaction mixture under vacuum and collected in a liquid nitrogen trap. Gas chromatograph mass spectroscopy (GCMS) analysis of the resulting liquid showed a high concentration of hexamethyldisilazane, indicating that the deprotonation of the pyrrole had proceeded as desired. The remaining solid reaction mixture was then subjected to sublimation at 150° C. to yield a colorless waxy solid (0.5 g), which was sublimed again under the same conditions to give 0.4 g (77% yield). NMR analysis and a positive flame test for barium showed this to be the THF free barium complex barium bis(2,3,5-tri-tert-butylpyrrolyl).
$^1$H NMR: (500 MHz, $C_6D_6$): δ=1.3 (m, 8H), δ=1.45 (s, 36H), δ=3.5 (m, 8H), δ=6.3 (s, 4H).

Example 6

Figure 4:
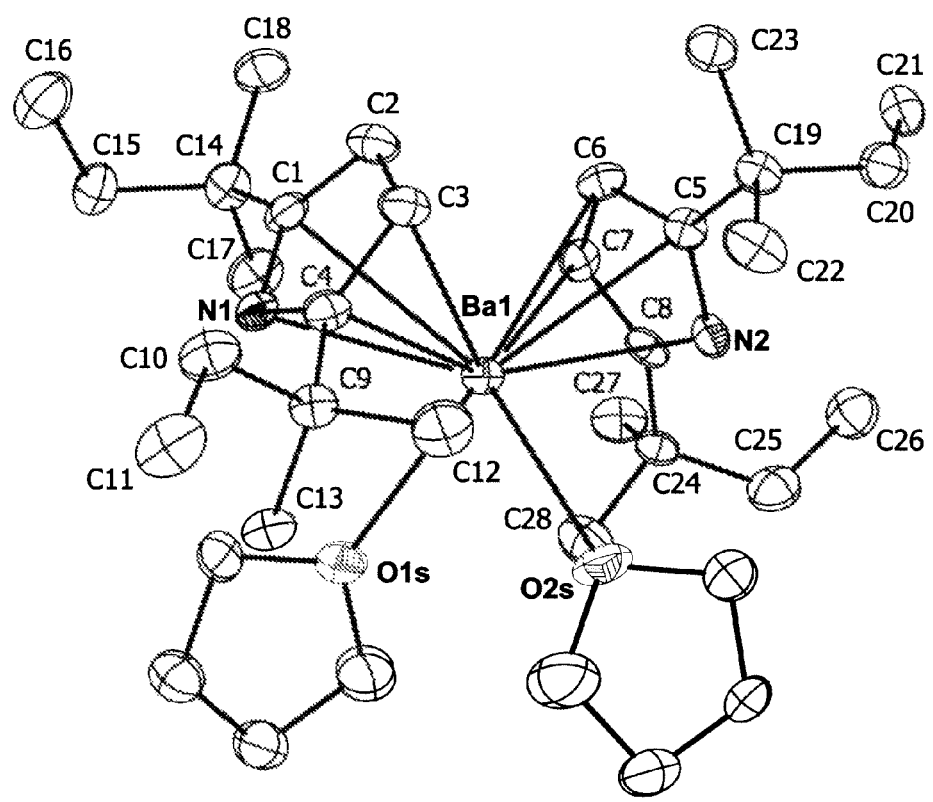
FIG. 4 barium bis(2,5-di-tert-amylpyrrolyl) bis tetrahydrofuran of Formula A as a monomer, no hydrogen atoms are shown.

Synthesis of barium bis(2,5-di-tert-amylpyrrolyl)$(THF)_2$ in FIG. 4

Under a nitrogen atmosphere, 20.7 g (0.1 moles) of 2,5-di-tert-amylpyrrole was dissolved with stirring in 125 ml of dry deoxygenated THF at room temperature. 30 g (0.05 moles) of barium hexamethyldisilazide $(THF)_2$ dissolved in 20 ml THF were added over 10 minutes and the mixture was allowed to stir overnight. The solvent and volatiles were then removed from this reaction mixture. The remaining solid reaction mixture (28.3 g) was recrystallized from hexane to yield the final product as colorless prisms, characterized by X-ray diffraction, as shown in FIG. 4

Example 7

Synthesis of di-barium tetrakis(2,5-di-tert-butylpyrrolyl) in FIG. 5

0.5 g of barium bis(2,5-di-tert-butylpyrrolyl) bis tetrahydrofuran were sublimed under dynamic vacuum at 175 C/50 mTorr to yield 0.35 g of di-barium tetrakis(2,5-di-tert-butylpyrroly) as colorless prisms (Yield of 92% based on barium bis(2,5-di-tert-butylpyrrolyl) bis tetrahydrofuran).
$^1$H NMR: (500 MHz, $C_6D_6$): δ=1.51 (s, 72H), δ=6.47 (s, 8H).

Example 8

Synthesis of di-barium tetrakis(2,5-di-tert-Amylpyrrolyl) in FIG. 6

The 28.3 g of crude barium bis(2,5-di-tert-Amylpyrrolyl)$(THF)_2$ from example 6 was sublimed at 150 C to yield the product di-barium tetrakis(2,5-di-tert-Amylpyrrolyl) as a white solid, 17 g (59% yield).
$^1$H NMR: (500 MHz, $C_6D_6$): δ=0.86 (t, 24H), δ=1.3 (s, 48H), δ=1.4 (q, 16H), δ=6.2 (s, 8H).

Example 9

Synthesis of di-strontium tetrakis(2,5-di-tert-amylpyrrolyl) in FIG. 7

Under a nitrogen atmosphere, 2.07 g (0.01 moles) of 2,5-di-tert-amylpyrrole was dissolved with stirring in 25 ml of dry deoxygenated THF at room temperature and then added to 0.4 g (0.01 moles) of potassium hydride stirred in 10 ml of tetrahydrofuran. This mixture was stirred for two hours to permit the deprotonation of the pyrrole with liberation of hydrogen to be complete. This solution was then added dropwise to a solution of 1.7 g (0.005 moles) of strontium iodide dissolved in 50 ml of tetrahydrofuran resulting in a white precipitate of potassium iodide. This mixture was stirred overnight, filtered and the solvent removed by vacuum. The resulting product was then sublimed at 150 C to yield 2.0 g (80% yield) of final product as colorless crystals.
$^1$H NMR: (500 MHz, $C_6D_6$): δ=0.77 (t, 24H), δ=1.33 (s, 48H), δ=1.61 (q, 16H), δ=6.25 (s, 8H).

FIG. 4, shows a mode of coordination of the pyrrolyl ligand to barium or other alkaline earth metals previously unreported in the chemical literature. In this mode, two of the pyrrolyl ligands of one compound of FIG. 1 (less the THF) bind to two barium ions each. One barium ion is bound in a distorted eta-5 type of coordination, while the other barium is bound in a sigma type donor bond to the nitrogen of the pyrrolyl anion. In this way, these two pyrrolyl ligands and two barium ions form a novel four membered ring. The other two pyrrolyl ligands bind to barium in the usual eta-5 mode. Thus, the chemical structure of the barium compound of FIG. 5 is without precedent in the chemical literature, and thus constitutes a new composition of matter.

Example 10

This example describes an ALD deposition of BaO using liquid delivery of 0.05M di-barium tetrakis(2,5-di-tert-butylpyrrolyl) is dissolved in solvent 2,2'-oxybis(N,N-dimethylethanamine). The deposition temperature range is 200~450° C. The deposition chamber pressure ranges around 1.5 Torr.

1. Introduce the barium precursor via liquid injection with Ar as carrier gas;
2. Ar purge to remove away any unsorbed barium precursor with Ar;
3. Introduce ozone into the deposition chamber, and;
4. Ar purge to remove away any unreacted ozone with Ar.

In this example, BaO films are obtained, showing a deposition temperature dependence of the resulting BaO film. The typical ALD conditions are: Ba precursor pulse time was 6 seconds, the Ar purge time after Ba precursor pulse was 10 seconds, the ozone pulse time was 5 seconds, and the Ar purge time after ozone pulse was 10 seconds. The cycle is repeated 50 times.

Figure 12:
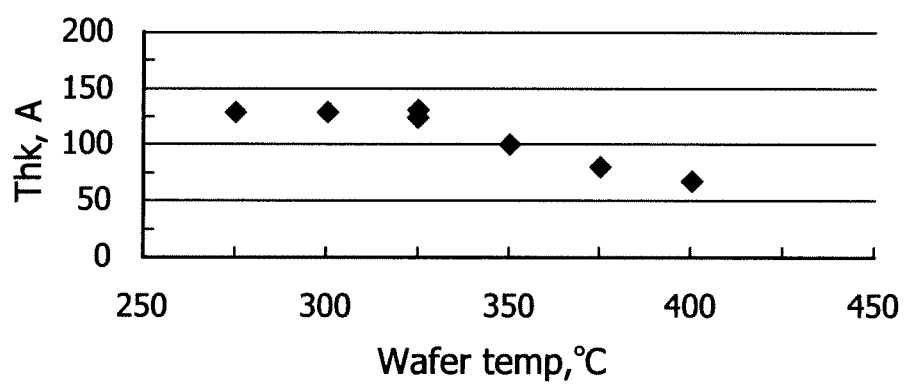
FIG. 12 is a graph of thickness vs temperature for atomic layer deposition of BaO using precursor/solvent combination of 0.05M di-barium tetrakis(2,5-di-tert-butylpyrrolyl) dissolved in solvent 2,2'-oxybis(N,N-dimethylethanamine). The data shows thickness measurements for 50 cycles of ALD pulsing deposition where the vaporizer temperature was 210 C, the liquid flow rate was 0.05 g/min, the liquid pulse time was 6 s, purge time 10 s, and ozone pulse time of 5 s.
Figure 13:
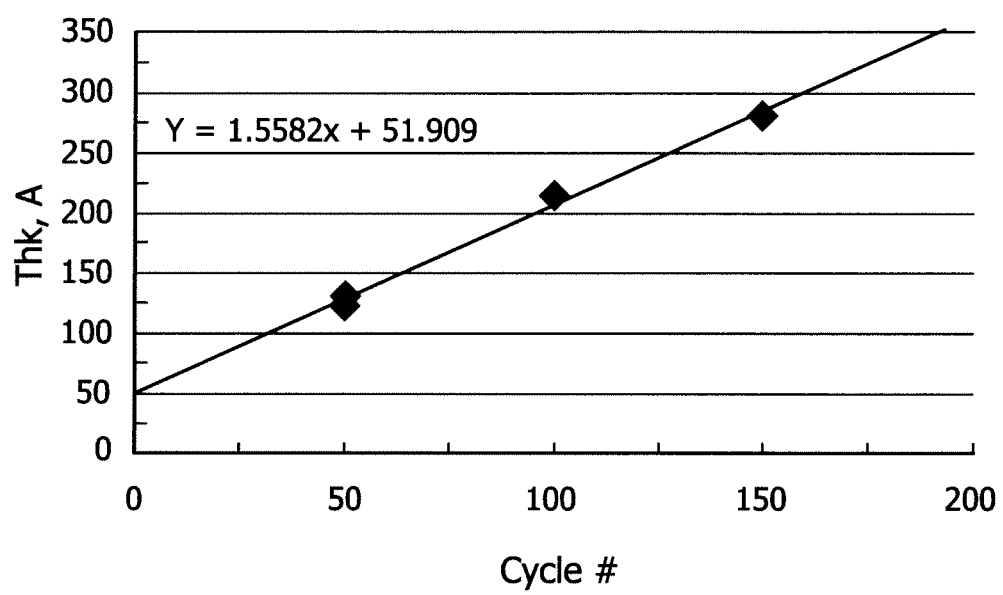
FIG. 13 is a graph demonstrating the ALD linearity of BaO formation with varied number of cycles; the plot shows the dependence of BaO thickness with varied number of cycles. The slope of the line identifies the deposition rate which was calculated to be 1.56 Å/cycle.

The results are depicted in FIG. 12 in which the ALD process window was up to ~325° C. Interestingly, the ALD window above 325° C. may still exist but at higher temperatures, the surface reaction kinetics reduce the desorption. This example highlights the viability of these precursors over a fairly large ALD window which is especially advantageous when forming a combined film, such as STO, BST, or BTO, where the ALD windows are needed to overlap. Particularly advantageous for this type of precursor is the reactivity observed which is demonstrated in FIG. 13 where the deposition rate was calculated to be 1.56 Å/cycle at a wafer temperature of 325° C.

The invention claimed is:

1. A compound having the following formula:

Formula B/C

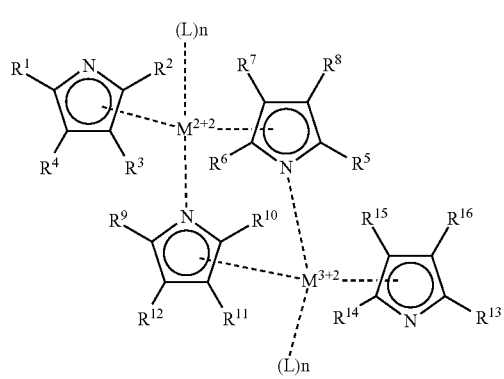

where $R^1$-$R^{16}$ are each individually acyl; formyl; amido; nitro; H; $C_1$-$C_{10}$ primary, secondary or tertiary alkyl; $C_1$-$C_{10}$ alkoxy; alkylamine; $C_1$-$C_{10}$ alkyl functionalized with a heteroatom substituted ring structure selected from the group consisting of imidazole, pyrrole, pyridine, furan, pyrimidine, pyrazole; $C_1$-$C_{10}$ alkyl functionalized with an amide group; $C_1$-$C_{10}$ alkyl functionalized with an ester group and mixtures thereof; wherein (L) is a neutral ligand individually selected from the group consisting of aliphatic $C_1$-$C_{20}$ ether or polyether; crownether; amine; poly amine; amide; poly amide; ester; polyester; aromatic ether; aromatic ester; aromatic amide; aromatic amine; pyridine; imidazole; pyridine; pyrazine; furan; pyrrole and mixtures thereof; $M^2$ and $M^3$ are individually selected from the group consisting of Ba, Sr, Ca, Ra or Mg; and each n independently=0-4.

2. The compound of claim 1 wherein R groups of one pyrrolyl anion are joined to the R groups of another pyrrolyl anion to connect the two anions together.

3. The compound of claim 1 having Formula B/C wherein $R^1$ to $R^{16}$ are each individually selected from the group consisting of H, tert-butyl, and tert-amyl; and M2 and M3 are individually selected from Ba or Sr.

4. The compound of claim 3 where $R^1$ to $R^{16}$ groups of pyrrolyl anions are joined to another $R^1$ to $R^{16}$ groups of pyrrolyl anions to connect the two anions together.

5. The compound of claim 3 selected from the group consisting of di-barium tetrakis(2,5-di-tert-butylpyrrolyl), di-strontium tetrakis(2,5-di-tent-amylpyrrolyl), and di-barium tetrakis(2,5-di-tert-amylpyrrolyl).

6. The compound of claim 5 comprising di-barium tetrakis(2,5-di-tert-butylpyrrolyl).

7. The compound of claim 5 comprising di-strontium tetrakis(2,5-di-tert-amylpyrrolyl).

8. The compound of claim 5 comprising di-barium tetrakis(2,5-di-tert-amylpyrrolyl).

9. A composition comprising a compound of claim 5 dissolved in at least one solvent selected from the group consisting of: an aliphatic hydrocarbon, an aromatic hydrocarbon, an aminoether, an ether, an ester, a nitrite, an amine, an organic amide, an alcohol, an imine, a carbodiimide, a ketone, an aldehyde, an amidine, a guandadine, an isourea, a glyme solvent having from 1 to 20 ethoxy —($C_2H_4O$)— repeat units, an aminoether and mixtures thereof.

10. The composition of claim 9 comprising wherein the solvent is 2,2'-oxybis(N,N-dimethylethanamine) and the compound dissolved therein is di-barium tetrakis(2,5-di-tert-butylpyrrolyl).

11. A method of depositing a metal containing film by reacting a compound of claim 1 with an oxidant selected from the group consisting of water, alcohol, oxygen, ozone, nitrous oxide, nitrogen dioxide, hydrogen peroxide or combinations thereof to grow a metal containing film selected from the group consisting of barium oxide, strontium oxide, magnesium oxide, calcium oxide or radium oxide and mixtures thereof, using a reactor pressure between 0.001-1000 Torr and a temperature from 0-1000° C.

* * * * *

UNITED STATES PATENT AND TRADEMARK OFFICE
CERTIFICATE OF CORRECTION

PATENT NO. : 8,859,785 B2
APPLICATION NO. : 12/785041
DATED : October 14, 2014
INVENTOR(S) : John Anthony Thomas Norman It is certified that error appears in the above-identified patent and that said Letters Patent is hereby corrected as shown below:

In The Claims

Column 18, Claim 5, line 3, delete the word "tent" in the formula and insert the word -- tert --.

Signed and Sealed this
Twelfth Day of May, 2015

Michelle K. Lee
*Director of the United States Patent and Trademark Office*